(12) United States Patent
Liang et al.

(10) Patent No.: US 9,959,615 B2
(45) Date of Patent: May 1, 2018

(54) SYSTEM AND METHOD FOR AUTOMATIC PULMONARY EMBOLISM DETECTION

(71) Applicants: Jianming Liang, Scottsdale, AZ (US); Nima Tajbakhsh, Tempe, AZ (US)

(72) Inventors: Jianming Liang, Scottsdale, AZ (US); Nima Tajbakhsh, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 21 days.

(21) Appl. No.: 15/200,742

(22) Filed: Jul. 1, 2016

(65) Prior Publication Data

US 2017/0004619 A1    Jan. 5, 2017

Related U.S. Application Data

(60) Provisional application No. 62/187,720, filed on Jul. 1, 2015.

(51) Int. Cl.
   *G06K 9/00*       (2006.01)
   *G06T 7/00*       (2017.01)
   (Continued)

(52) U.S. Cl.
   CPC ........ *G06T 7/0012* (2013.01); *A61B 5/02007* (2013.01); *A61B 6/032* (2013.01); *A61B 6/504* (2013.01); *A61B 6/5211* (2013.01); *A61B 6/5223* (2013.01); *A61B 8/0891* (2013.01); *G06K 9/4628* (2013.01); *G06K 9/6272* (2013.01); *A61B 5/055* (2013.01); *G06K 2209/05* (2013.01); *G06T 2207/20084* (2013.01); *G06T 2207/30061* (2013.01);
   (Continued)

(58) Field of Classification Search
   None
   See application file for complete search history.

(56) References Cited

U.S. PATENT DOCUMENTS 9,449,381 B2    9/2016  Liang
2005/0100208 A1*  5/2005  Suzuki ................... G06T 5/007
                                                      382/157

(Continued)

OTHER PUBLICATIONS

Alexandre, L., "Color and Position versus Texture Features for Endoscopic Polyp Detection", 2008 International Conference on BioMedical Engineering and Informatics, May 27-30, 2008, 2008, 2:38-42.

(Continued)

*Primary Examiner* — Atiba O Fitzpatrick
(74) *Attorney, Agent, or Firm* — Byrne Poh LLP (57) ABSTRACT

A system and method for detecting pulmonary embolisms in a subject's vasculature are provided. In some aspects, the method includes acquiring a set of images representing a vasculature of the subject, and analyzing the set of images to identify pulmonary embolism candidates associated with the vasculature. The method also includes generating, for identified pulmonary embolism candidates, image patches based on a vessel-aligned image representation, and applying a set of convolutional neural networks to the generated image patches to identify pulmonary embolisms. The method further includes generating a report indicating identified pulmonary embolisms.

16 Claims, 7 Drawing Sheets

(51) Int. Cl.
<table>
<tr><td>A61B 5/02</td><td>(2006.01)</td></tr>
<tr><td>A61B 6/03</td><td>(2006.01)</td></tr>
<tr><td>A61B 6/00</td><td>(2006.01)</td></tr>
<tr><td>A61B 8/08</td><td>(2006.01)</td></tr>
<tr><td>G06K 9/62</td><td>(2006.01)</td></tr>
<tr><td>G06K 9/46</td><td>(2006.01)</td></tr>
<tr><td>A61B 5/055</td><td>(2006.01)</td></tr>
</table>

(52) U.S. Cl.
CPC ............... *G06T 2207/30101* (2013.01); *G06T 2207/30172* (2013.01)

(56) References Cited

U.S. PATENT DOCUMENTS

<table>
<tr><td>2008/0192887 A1</td><td>8/2008</td><td>Weese et al.</td></tr>
<tr><td>2009/0034816 A1</td><td>2/2009</td><td>Ghanem et al.</td></tr>
<tr><td>2009/0060307 A1</td><td>3/2009</td><td>Ghanem et al.</td></tr>
<tr><td>2009/0252394 A1</td><td>10/2009</td><td>Liang et al.</td></tr>
<tr><td>2010/0046815 A1</td><td>2/2010</td><td>Von Berg et al.</td></tr>
<tr><td>2010/0061601 A1</td><td>3/2010</td><td>Abramoff et al.</td></tr>
<tr><td>2012/0106815 A1</td><td>5/2012</td><td>Yang et al.</td></tr>
<tr><td>2014/0072191 A1</td><td>3/2014</td><td>Liang et al.</td></tr>
<tr><td>2016/0321427 A1*</td><td>11/2016</td><td>Bogoni ............... G06F 19/3443</td></tr>
</table>

OTHER PUBLICATIONS

An, Y. et al., "Novel Chance-Constrained Optimization in Intensity-Modulated Proton Therapy Planning to Account for Range and Patient Setup Uncertainties", Medical Physics, Jun. 2015, 42(6):3467-3468.

Bernal, J. et al., "Towards automatic polyp detection with a polyp appearance model", Pattern Recognition, Sep. 2012 (available online Mar. 2012), 45(9):3166-82.

Bouma, H. et al., "Automatic Detection of Pulmonary Embolism in CTA Images", IEEE Transactions on Medical Imaging, Aug. 2009 (available online Feb. 2009), 28(8)1223-30.

CAD-PE Challenge, "Pulmonary Embolism", <http://www.cad-pe.org/>, screenshot obtained on Jul. 21, 2016.

Ciresan, D. et al., "Mitosis detection in breast cancer histology images with deep neural networks", MICCAI 2013 (16th International Conference, Sep. 22-26, 2013), Lecture Notes in Computer Science (including subseries Lecture Notes in Artificial Intelligence and Lecture Notes in Bioinformatics), 2013, vol. 8150, pp. 411-8.

Das, M. et al., "Computer-aided detection of pulmonary embolism: Influence on radiologists' detection performance with respect to vessel segments", European Radiology, Jul. 2008 (available online Feb. 2008), 18(7):1350-1355.

Frangi, A. et al., "Model-Based Quantitation of 3-D Magnetic Resonance Angiographic Images", IEEE Transactions on Medical Imaging, Oct. 1999, 18(10), pp. 946-956.

Karkanis, S. et al., "Computer-Aided Tumor Detection in Endoscopic Video Using Color Wavelet Features", IEEE Transactions on Information Technology in Biomedicine, Sep. 2003, 7(3):141-52.

Krizhevsky, A. et al., "ImageNet Classification with Deep Convolutional Neural Networks", Advances in Neural Information Processing Systems (NIPS'12 Proceedings of the 25th International Conference on Neural Information Processing Systems, Dec. 3-6, 2012), 2012, 2:1097-105.

Leufkens, A. et al., "Factors influencing the miss rate of polyps in a back-to-back colonoscopy study", Endoscopy, May 2012 (available online Mar. 2012), 44(5):470-5.

Liang, J. et al., "Computer Aided Detection of Pulmonary Embolism with Tobogganing and Mutiple Instance Classification in CT Pulmonary Angiography", Information Processing in Medical Imaging, Lecture Notes in Computer Science (including subseries Lecture Notes in Artificial Intelligence and Lecture Notes in Bioinformatics), 2007, vol. 4584, pp. 630-41.

Liang, J. et al., "Local characteristic features for computer aided detection of pulmonary embolism in ct angiography", Proceedings of Pulmonary Image Analysis at Annual Conference on Medical Image Computing and Computer Assisted Intervention, 2008, 9 pages.

Lieberman, D., "Quality and colonoscopy: a new imperative", Gastrointestinal Endoscopy, Mar. 2005, 61(3):392-4.

Office Action, dated Apr. 24, 2015, U.S. Appl. No. 14/023,380.

Office Action, dated Jan. 4, 2016, U.S. Appl. No. 14/023,380.

Ozkan, H. et al., "A novel method for pulmonary embolism detection in CTA images", Computer Methods and Programs in Biomedicine, Mar. 2014 (available online Dec. 2013), 113(3):757-66.

Park, S. et al., "A Colon Video Analysis Framework for Polyp Detection", IEEE Transactions on Biomedical Engineering, May 2012 (available online Feb. 2012), 59(5)1408-18.

Park, S. et al., "A Multistage Approach to Improve Performance of Computer-Aided Detection of Pulmonary Embolisms Depicted on CT Images: Preliminary Investigation", IEEE Transactions on Biomedical Engineering, Jun. 2011 (available online Aug. 2010), 58(6):1519-27.

Prasoon, A. et al., "Deep feature learning for knee cartilage segmentation using a triplanar convolutional neural network" MICCAI 2013 (16th International Conference, Sep. 22-26, 2013), Lecture Notes in Computer Science (including subseries Lecture Notes in Artificial Intelligence and Lecture Notes in Bioinformatics), 2013, vol. 8150, pp. 246-53.

Rabeneck, L. et al., "Outcomes of colorectal cancer in the United States: no change in survival (1986-1997)", American Journal of Gastroenterology, Feb. 2003, 98:471-77.

Roth, H. et al., "A new 2.5D representation for lymph node detection using random sets of deep convolutional neural network observations", MICCAI 2014 (17th International Conference, Sep. 14-18, 2014), Lecture Notes in Computer Science (including subseries Lecture Notes in Artificial Intelligence and Lecture Notes in Bioinformatics), 2014, vol. 8673, pp. 520-7.

Shin, J. et al., "Effective Dose-Volume-Histogram Prediction Method Using Euclidean Distance Volume Histogram for Volumetric Modulated Arc Therapy to Treat Prostate Cancer", Medical Physics, Jun. 2015, 42(6):3413.

Tajbakhsh, N. et al., "A classification-enhanced vote accumulation scheme for detecting colonic polyps", Abdominal Imaging: Computation and Clinical Applications (5th International Workshop Held in Conjunction with MICCAI 2013, Sep. 22, 2013), Lecture Notes in Computer Science (including subseries Lecture Notes in Artificial Intelligence and Lecture Notes in Bioinformatics), 2013, vol. 8198, pp. 53-62.

Tajbakhsh, N. et al.,"A Comprehensive Computer-Aided Polyp Detection System for Colonoscopy Videos", Information Processing in Medical Imaging, Jun. 2015, Lecture Notes in Computer Science 9123:327-38, Springer.

Tajbakhsh, N. et al., "Automated Polyp Detection in Colonoscopy Videos Using Shape and Context Information", IEEE Transactions on Medical Imaging, Feb. 2016 (available online Oct. 2015), 35(2):630-44.

Tajbakhsh, N. et al., "Automatic polyp detection in colonoscopy videos using an ensemble of convolutional neural networks", 2015 IEEE 12th International Symposium on Biomedical Imaging (ISBI) (Apr. 16-19, 2015), 2015, 79-83.

Tajbakhsh, N. et al., "Automatic polyp detection using global geometric constraints and local intensity variation patterns", MICCAI 2014 (17th International Conference, Sep. 14-18, 2014,), Lecture Notes in Computer Science (including subseries Lecture Notes in Artificial Intelligence and Lecture Notes in Bioinformatics), 2014, vol. 8674, pp. 179-87.

Tajbakhsh, N. et al., "Computer-aided pulmonary embolism detection using a novel vessel-aligned multi-planar image representation and convolutional neural networks", MICCAI 2015 (18th International Conference, Oct. 5-9, 2015), Lecture Notes in Computer Science (including subseries Lecture Notes in Artificial Intelligence and Lecture Notes in Bioinformatics), Nov. 2015, vol. 9350, pp. 62-69.

Wang, X. et al., "Improving performance of computer-aided detection of pulmonary embolisms by incorporating a new pulmonary (56) References Cited

OTHER PUBLICATIONS vascular-tree segmentation algorithm", Proceedings of SPIE, Medical Imaging, International Society for Optics and Photonics, Feb. 2012, pp. 83152U (8 pages).
Wang, Y. et al., "Part-Based Multiderivative Edge Cross-Sectional Profiles for Polyp Detection in Colonoscopy", IEEE Journal of Biomedical and Health Informatics, Jul. 2014 (available online Oct. 2013), 18(4)1379-89.

* cited by examiner

SYSTEM AND METHOD FOR AUTOMATIC PULMONARY EMBOLISM DETECTION

CROSS-REFERENCE TO RELATED APPLICATIONS

This application is based on, claims priority to, and incorporates herein by reference in its entirety U.S. Provisional Application Ser. No. 62/187,720, filed Jul. 1, 2015, and entitled "VESSEL-ALIGNED MULTI-PLANAR IMAGE REPRESENTATION FOR AUTOMATED PULMONARY EMBOLISM DETECTION WITH CONVOLUTIONAL NEURAL NETWORKS."

BACKGROUND

The present disclosure relates, generally, to systems and method for processing optical images. More particularly, the disclosure relates to automatic detection of pulmonary embolisms using images.

Pulmonary embolisms ("PEs") are blood clots that travels from the legs, or other parts of the body, to the lungs. In the lungs, blood clots can block central, lobar, segmental, or sub-segmental pulmonary arteries, depending on its size. If left undiagnosed, PEs lead to a mortality rate of up to 30%. However, with early diagnosis and treatment, the mortality rate can be reduced to less than 11%.

The primary imaging technique utilized for PE diagnosis is computed tomography pulmonary angiogram ("CTPA"). In CTPA, an embolus appears as a dark region surrounded by the brighter vessel lumen. Interpreting a CTPA dataset demands a radiologist to carefully trace each branch of the pulmonary vasculature for any suspected PEs. However, with a large number of arteries to be tracked and complexity of the images, PE diagnosis often requires extensive reading time whose accuracy depends on a clinician's experience, attention span, eye fatigue, as well as sensitivity to the visual characteristics of different PEs.

Computer-aided detection ("CAD") can play a major role in helping clinicians diagnose PEs. In particular, recent clinical studies have shown that CAD systems can increase sensitivity to identifying PEs. However, despite a demonstrated utility, existing CAD technologies still produce relatively high false positives in order to achieve clinically acceptable PE sensitivity. Such high number of false positives, generated by CAD systems, prolong the reading time of CTPA studies because each PE candidate must be examined by a radiologist.

Therefore, in light of the above, there is a clear need for improved systems and methods for detecting pulmonary embolisms that can achieve higher sensitivity at a clinically acceptable false positive range.

SUMMARY

The present disclosure overcomes the aforementioned drawbacks by providing a system and methods for detecting pulmonary embolisms using images. In addition, the present disclosure overcomes the shortcomings of previous technologies by providing a novel approach for reducing false positives around non-pulmonary embolus ("PE") structures implementing convolutional neural networks ("CNNs") and a vessel-aligned image representation.

In one aspect of the disclosure, a system for detecting pulmonary embolisms in a subject's vasculature is provided. The system includes an input configured to receive images acquired from a subject, and a processor configured to process the images with steps comprising receiving, using the input, a set of images representing a vasculature of the subject, analyzing the set of images to identify pulmonary embolism candidates associated with the vasculature, and generating, for identified pulmonary embolism candidates, image patches based on a vessel-aligned image representation. The processor is also configured to carry out steps for applying a set of convolutional neural networks to the generated image patches to identify pulmonary embolisms, and generating a report indicating identified pulmonary embolisms. The system also includes an output for displaying the report.

In another aspect of the disclosure, a method for detecting pulmonary embolisms in a subject's vasculature is provided. The method includes acquiring a set of images representing a vasculature of the subject, and analyzing the set of images to identify pulmonary embolism candidates associated with the vasculature. The method also includes generating, for identified pulmonary embolism candidates, image patches based on a vessel-aligned image representation, and applying a set of convolutional neural networks to the generated image patches to identify pulmonary embolisms. The method further includes generating a report indicating identified pulmonary embolisms.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

Other aspects and advantages of the present disclosure will become apparent upon consideration of the following detailed description and attached drawings.

DETAILED DESCRIPTION

Computer-based techniques can be tremendously helpful in diagnosing pulmonary embolisms ("PEs"), reducing the rate of PEs missed by an examining clinician. In general, existing detection systems operate by 1) extracting a volume of interest ("VOI") from an imaging dataset, such as computed tomography pulmonary angiogram ("CTPA") imaging data, by performing lung or vessel segmentation, 2) generating a set of PE candidates within the VOI using algorithms, such as tobogganing, 3) extracting features from each PE candidate, and 4) computing a confidence score for each of the candidates. Due to advances in development of robust segmentation methods, most existing systems can achieve acceptable sensitivity to PEs in stages 1 and 2. However, such systems do not perform desirably in the subsequent stages where the goal is to remove as many false positives as possible given a set of PE candidates. As a result, these systems either produce too many false positives in order to achieve a high enough detection sensitivity, or yield acceptable false positive rates and settle for limited sensitivity levels. An inadequate modeling of PEs based on fragile and hand-crafted features, as well as other reasons, may cause further sub-optimal performance. As such, achieving clinical necessary sensitivity with an acceptable number of false positives, say between 1 to 5 false positives per CTPA study), requires capabilities not currently possible.

Therefore, the present disclosure provides a system and method that overcomes the shortcomings of existing technologies. In particular, disclosed herein is a novel approach for identifying PEs that generally includes generating a set of PE candidates by applying, for example, a tobogganing algorithm to segmented lungs using a given imaging dataset. The essential context information around each identified PE candidate can then be efficiently captured by using a novel image representation, namely a vessel-aligned, multi-planar, image representation, as will be described. Non-PE candidates (false positives) can then be effectively distinguished from true PE candidates (true positives) by automatically learning discriminative features from the extracted vessel-aligned, multi-planar, representation using a convolutional neural network ("CNN") framework. As will be described, the present vessel-aligned multi-planar image representation offers several advantages, including efficiency and compactness, capable of concisely summarizing 3D contextual information in only 2 image channels. The representation also consistently aligns PE candidates according the orientation of the associated vessels, and is expandable because it naturally supports data augmentation for training a CNN.

Figure 1:
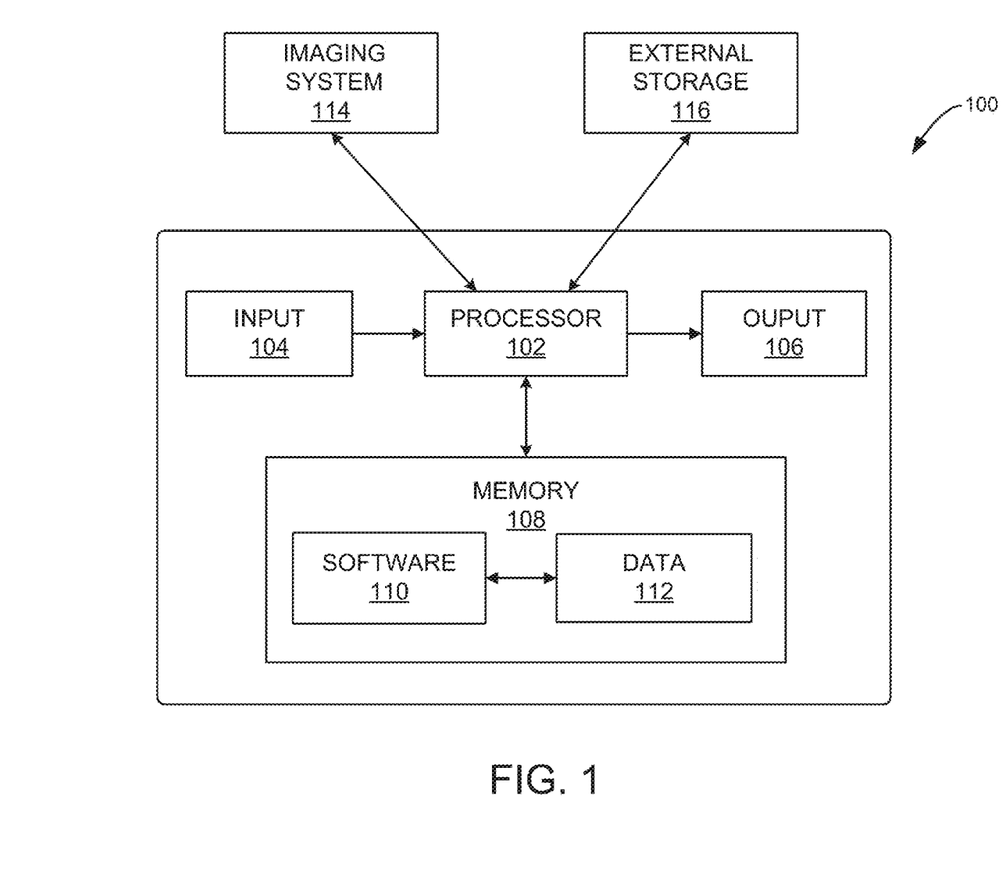
FIG. 1 is a schematic diagram of an example system for pulmonary embolism detection, in accordance with aspects of the present disclosure.

Turning now to FIG. 1, a block diagram of an example system 100 for detecting pulmonary embolisms in a subject's vasculature. The system 100 may generally include a processor 102, an input 104, an output 106, and a memory 108 having software 110 and data 112 stored therein. For example, the system 100 may be a workstation, a notebook computer, a personal digital assistant ("PDA"), a multimedia device, a network server, a mainframe or any other general-purpose or application-specific computing device. In some aspects, the system 100 may be portable, such as a mobile device, laptop, tablet, or other portable device or apparatus. The system 100 may operate as part of, or in collaboration with a computer, system, device, machine, mainframe, or server, and so forth. In this regard, the system 100 may be any computing device, apparatus or system configured for carrying out instructions in accordance with aspects of the present disclosure.

The system 100 may integrate a variety of software, hardware capabilities and functionalities, and operate autonomously or semi-autonomously. In some aspects, the system 100 may read executable instructions, stored in the memory 108 as transitory and/or non-transitory computer-readable media. The system 100 may also receive instructions, information or data from a user, or any other source logically connected thereto, such as another system, device, apparatus, networked computer, server, database, the internet, a cloud, and so forth.

In some implementations, as shown in FIG. 1, the processor 102 may be in communication with an imaging system 114 and/or an external storage 118, and configured to exchange a wide variety of data and information, including imaging data, therebetween. By way of example, the imaging system 114 may be a computed tomography ("CT") system, a fluoroscopy system, a magnetic resonance ("MR"), system, an ultrasound ("US") system, and so forth. The system 100 may be configured to acquire image data and analyze the data in substantially real-time. Alternatively, the system 100 may also be configured to access, retrieve and analyze image data already stored in memory 108, external storage 116, or other data location.

In addition to being configured to carry out steps for operating the system 100, the processor 102 may be configured to acquire and/or process image data, including image data obtained during a medical procedure, such as a pulmonary angiography. As such, the processor 102 may read and execute instructions stored on a non-transitory computer-readable medium. In particular, as will be described, the processor 102 may be configured to acquire or access image data, such as two-dimensional and/or three-dimensional CT pulmonary angiography data representing a vasculature of the subject, and analyze the image data to identify PE candidates associated with the vasculature. To this end, processor 102 may be configured to select pulmonary regions, using various segmentation techniques, and apply, for instance, a tobogganing algorithm to identify PE candidates. In some implementations, a user may provide various selections for different regions or volumes of interest associated with a subject's lungs using the input 104, such as a mouse, keyboard, touchpad, touch screen, buttons, and others.

In accordance with aspects of the disclosure, the processor 102 may transform acquired image data into a vessel-aligned multi-planar representation. As will be described, such representation affords many advantages, including consistent PE appearance that allows for accurate detection. For example, typical 3D CTPA data is usually provides axial, coronal and sagittal views with respect to an imaged patient. By contrast, upon estimating the orientation of vessels including PE candidates, the processor 102 may transform the imaging data into longitudinal and cross-sectional view of respective vessels. The processor 102 may then generate various image patches, using vessel-aligned image representation, and apply CNN to the generated image patches to identify pulmonary embolisms.

A report may then be generated by the processor 102, and provided via the output 106, which may include an audio and/or visual display system. The report may be provided either intermittently or in substantially real time, and may include a variety of information, including information associated with pulmonary embolisms detected. For example, the report may include CTPA images that highlight various regions or volumes of interest, including detected PE candidates and PEs, as well as non-PE structures, such as vessels, lungs, and other tissues or organs. The report may also indicate the probabilities or confidence scores for identified objects being PEs. The report may also include an audio alert or signal to an operator upon identification of PEs.

Figure 2:
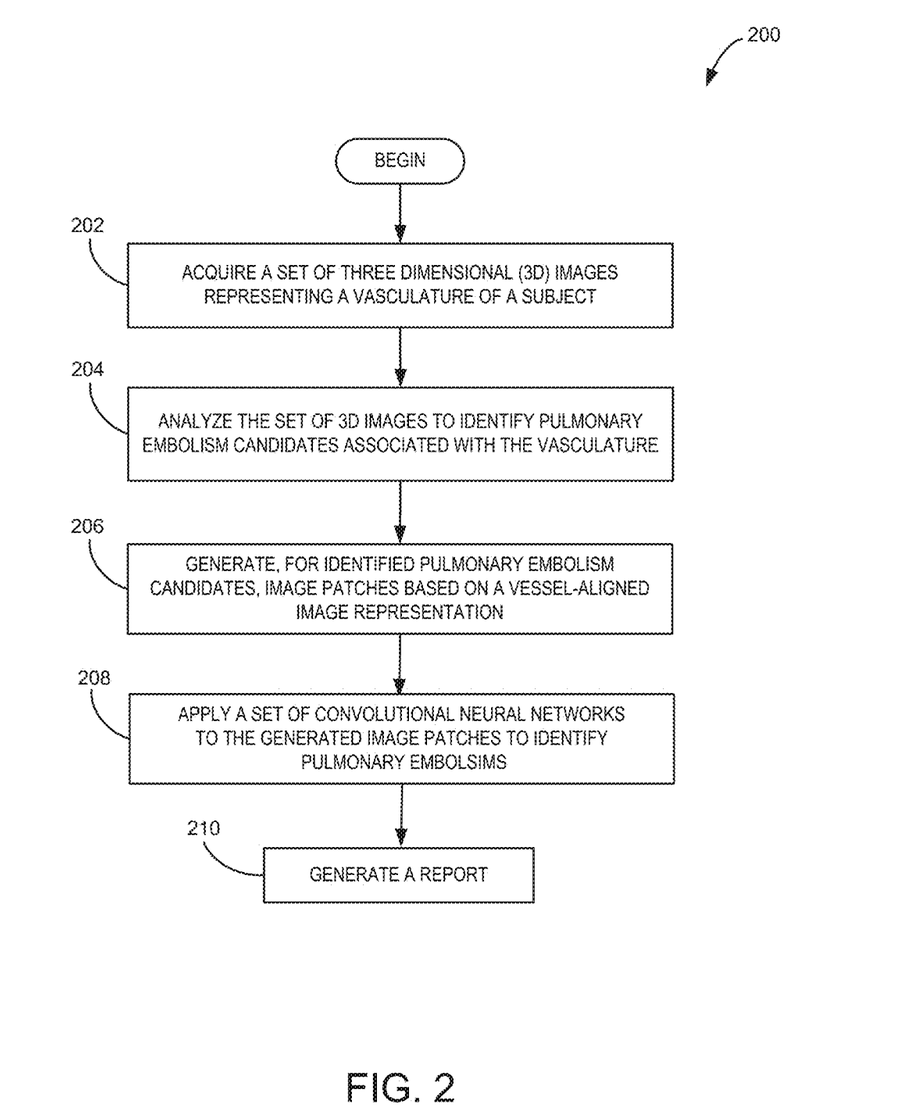
FIG. 2 is a flowchart setting forth steps of a process, in accordance with aspects of the present disclosure.

Turning now to FIG. 2, steps of a process 200, in accordance with aspects of the present disclosure, are shown. In some implementations, the process 200 may be carried out using a system 100 as described with respect to FIG. 1, as well as any other suitable system, device or apparatus. The process 200 may begin at process block 202 with acquiring or accessing image data, and in particular image data representing a subject's vasculature. In some aspects, the acquired image data may include a set of three-dimensional images, such as CTPA images. As described, the image data may be acquired using an imaging system, such as a CT imaging system. Alternatively, the image data may be accessed or retrieved from a data storage location, memory, database, cloud, imaging system and so forth.

At process block 204, an analysis identifying PE candidates associated with the subject's vasculature may be carried out using the acquired or accessed images. In one implementation, a tobogganing algorithm may be executed in order to identify the PE candidates. Other techniques may also be utilized. Also, a number of pre-processing steps may also be carried out at process block 204. For example, accessed or retrieved image data may be assembled into a set of images. In some aspects, a segmentation procedure may be carried out for identifying a subject's lungs, for example. In addition, images be transformed into a vessel-aligned, multi-planar, image representation, as will be described.

Figure 3:
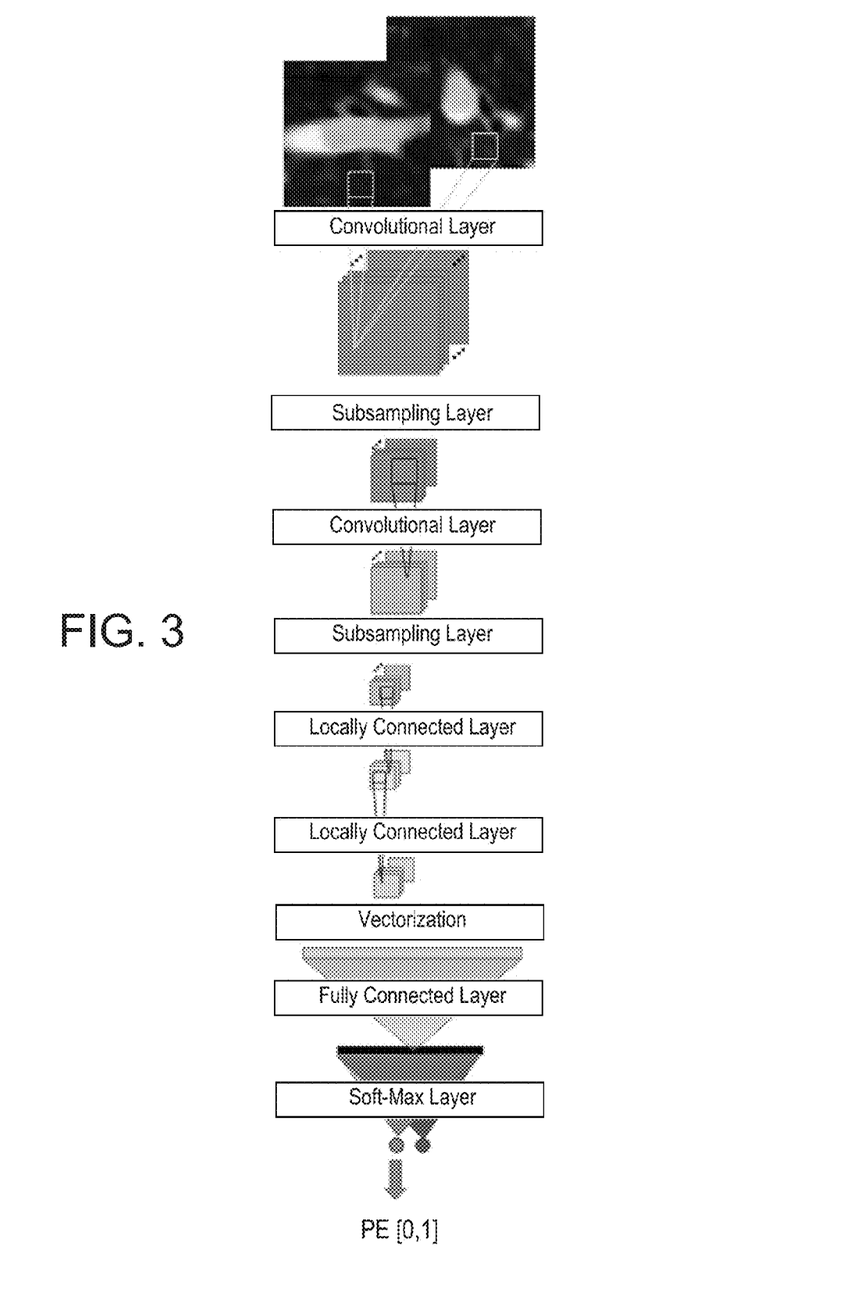
FIG. 3 is an illustration showing an example convolutional neural network layout, in accordance with the present disclosure.

Then, at process block 206, various image patches may be generated for identified PE candidates. As described, image patches based on a vessel-aligned multi-planar representation provide an advantageous presentation that allows for more accurate PE detection. Then, at process block 208, a CNN framework may be applied to the generated image patches to identify PEs. That is, the generated image patches may be fed into CNNs trained to classify underlying candidates into PE and non-PE categories. In some implementations, a GPU-based open source realization of CNNs with a layout, as shown in FIG. 3, can be used. More sophisticated network architectures could also be used, resulting in more computationally burden, but no significant performance gain. A confidence score, or probability may then be computed at process block 208. Subsequently, at process block 210, a report may then be generated. As described, the report may be indicative of identified PEs, their respective locations, along with confidence values or probabilities indicating the accuracy of detection.

Previous methods to address sources of false positives in automated PE detection systems have implemented a variety of hand-crafted features. As described, these approaches produce inferior results. By contrast, the present disclosure recognizes that CNNs may be effectively used to eliminate false positives associated with non-PE structures. In particular, CNNs are deep learning machines that eliminate the need for designing hand-crafted features because they learn the features while training a classifier simultaneously. Typically, a CNN consists of several pairs of convolutional and subsampling layers followed by locally connected layers, fully connected layer, and a final soft-max layer for classification, as illustrated in FIG. 3. Convolutional layers apply convolutional filters to the input channels, subsampling layers reduce the size of feature maps by say 50%, locally connected layers increase the discrimination power, fully connected layer powered by "DropConnect" can alleviate over fitting, and the soft-max layer ensures a probabilistic classification confidence.

The success of applying a CNN for object detection may rely on how to represent objects of interest, such as pulmonary embolisms. Although the choice of image representation may not be critical for 2D images, it has proven to be important when it comes to detecting objects in 3D volumetric datasets, such as CT images. Herein, it is recognized that a suitable 3D image representation for CNNs meets three requirements: (1) compactness and efficiency, (2) consistency across instances, and (3) expandability for data augmentation. To this end, the herein provided vessel-aligned multi-planar representation for PE, meets all three properties.

By way of example, generating a vessel-aligned multi-planar representation based upon 3D CT imaging is described below. As a first step, a vessel orientation is first determined. Let C denote a PE candidate in volume V and $S_C$ denote the PE segmentation or equivalently the set of voxels comprising a PE candidate. In one example, a 15×15×15 mm neighborhood $N_P$ around the PE candidate ($S_P \subset N_P$), may be first extracted. In the resulting subvolume, the PE appears as a filling defect because PEs are relatively darker than the containing vessel. To minimize the influence of the filling defect in vessel orientation estimation, a vessel-like intensity value of approximately 100 HU (Hounsfield unit) may be assigned to the PE voxels within the subvolume, $N_P(x, y, z)=100$ HU if $(x, y, z) \in S_P$. This has the effect of filling the hole (PE) in the vessel. The $N_P$ may be binarized with a threshold of approximately 100 HU, and the connected component containing the PE segmentation $S_C$ may be chosen. Because the selected component corresponds to the vessel, the vessel orientation may be obtained by applying an vessel orientation analysis—e.g., principle component analysis—to the voxels of the selected component. If $v_1$, $v_2$, $v_3$ denote the eigenvectors of the analyzed component ($\lambda_1 \geq \lambda_2 \lambda_3$), then interpolating the volume along $\{v_1, v_2\}$ or $\{v_1, v_3\}$ results in longitudinal view of the PE (the first channel of the image representation) and interpolating the volume along $\{v_2, v_3\}$ results in the cross-sectional view of the PE (the second channel in the image representation). Structure tensor or Hessian matrix can also be used to determine the vessel orientation.

The image representation described herein is compact because it concisely summarizes the 3D contextual information around PEs in only 2 views or image channels. While it is theoretically possible to train a CNN using subvolumes with an arbitrary number of slices, the performance of such networks have been reported to be inferior to the CNNs that have been trained using samples with a fewer number of slices. In fact, the information embedded in the additional image slices has been shown to degrade classification performance. This phenomenon is attributed to the curse of dimensionality where a large number of image channels correspond to learning a far larger number of network parameters, which in turn leads to over-fitting to the training samples and thus poor generalization performance. Even with techniques to avoid over-fitting, training CNNs using volumetric data requires very large datasets, which is significantly hindered by computational and storage resources. It is therefore desirable to efficiently represent the 3D context around the object of interest in a low dimensional image representation, as described herein.

In addition, the image representation described herein provides consistent appearance of the object of interest across multiple instances. In general, emboli can occur in pulmonary vessels in any orientation. As a result, they can appear very differently in the images acquired using traditional original axial, sagittal and coronal imaging planes. Such a significant appearance variation in the resulting patches presents serious complications for the classification task, resulting in the partial utilization of CNNs. Therefore, the provided image representation, having alignment with vessels, allows for a consistent image representation, where emboli consistently appear as an elongated structure in the longitudinal vessel view and as a circular structure in the cross-sectional vessel view.

Figure 4:
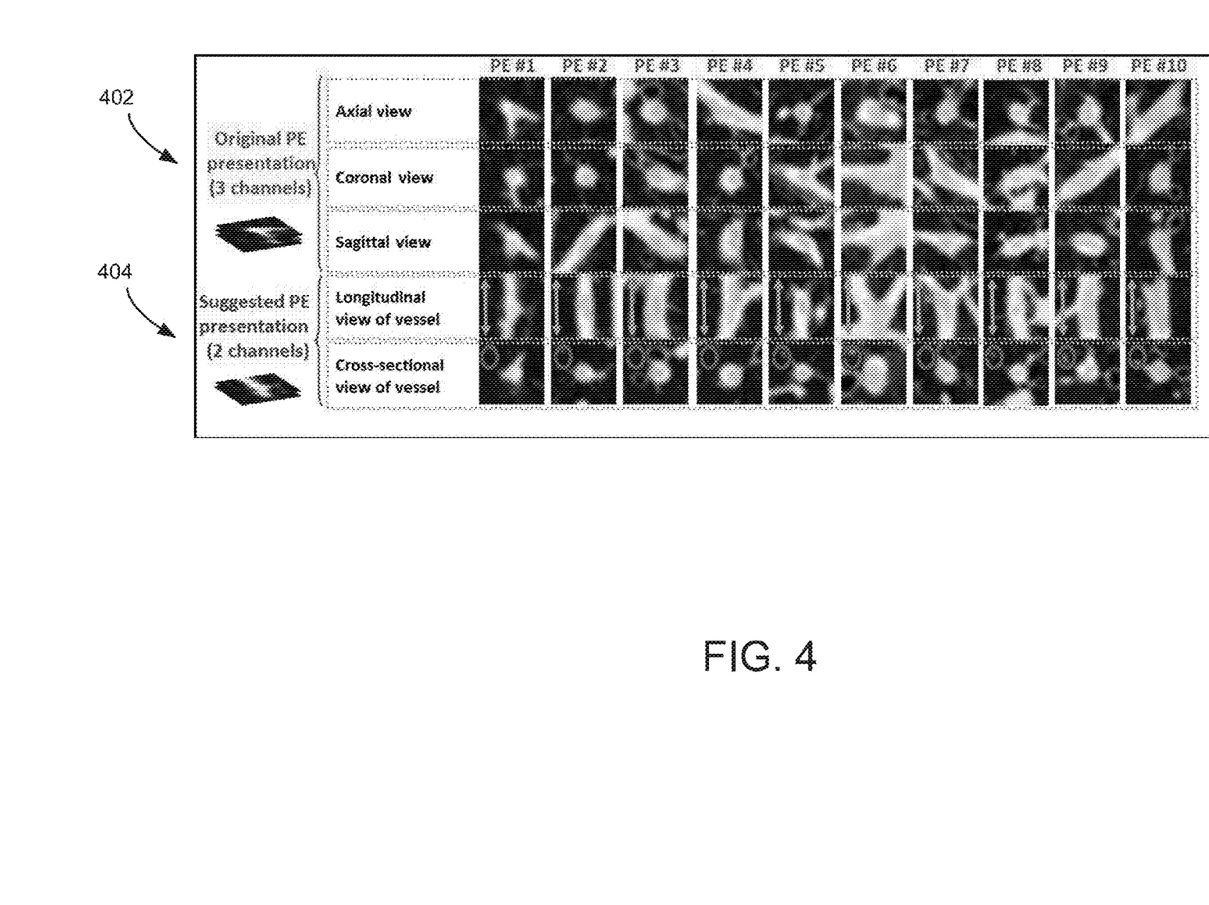
FIG. 4 is an illustration comparing the appearance of pulmonary embolisms using traditional imaging views and a vessel-aligned image representation, in accordance with aspects of the present disclosure.

By way of example, FIG. 4 illustrates variations in the appearances for a number PE using a traditional image representations 402 based on sagittal, coronal and axial views in comparison with the vessel-aligned image representation 404 described. As appreciated from FIG. 4, the vessel-aligned image representation 404 characterizes emboli more consistently than the original axial, sagittal, and coronal views. In particular, this approach consistently captures PEs and associated vessels as elongated and circular structures in the first and second channels, respectively. By contrast, 3-channel images representing sagittal, coronal and axial views do not provide this property. Given the varying orientations of the containing vessels, identification of possible PEs is much more difficult. As mentioned, the present disclosure recognizes that a consistent image appearance is the key to training an accurate image classifier.

Figure 5A:
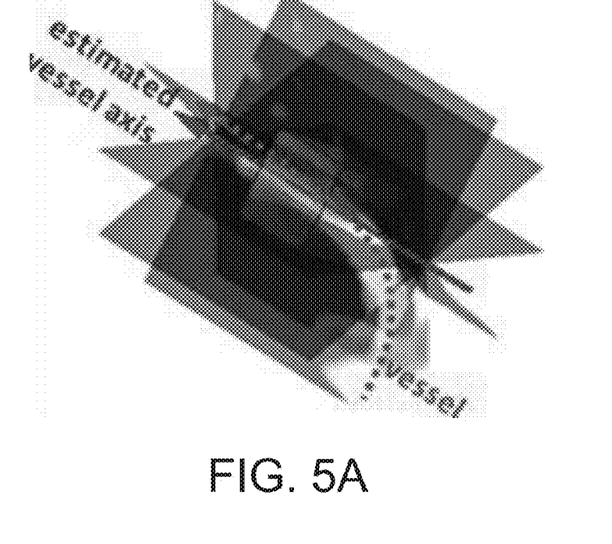
FIG. 5A is an illustration showing data augmentation using random rotation axes, in accordance with aspects of the present disclosure.
Figure 5B:
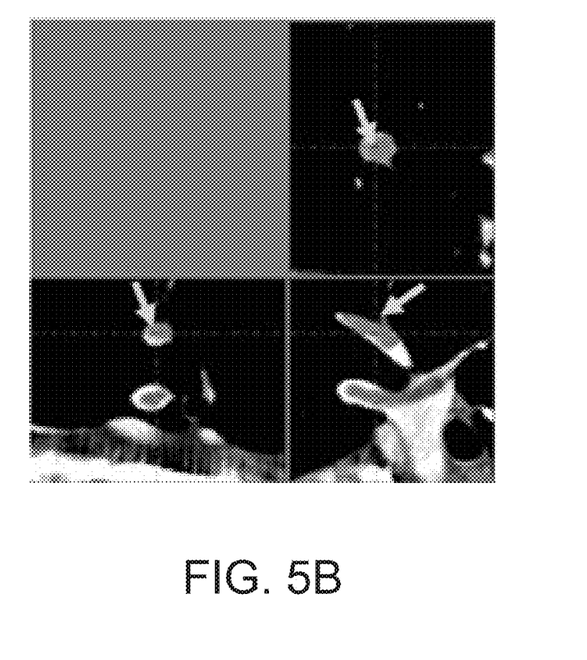
FIG. 5B is an illustration showing the use of two envelopes to achieve consistence for data augmentation, in accordance with aspects of the present disclosure.
Figure 5C:
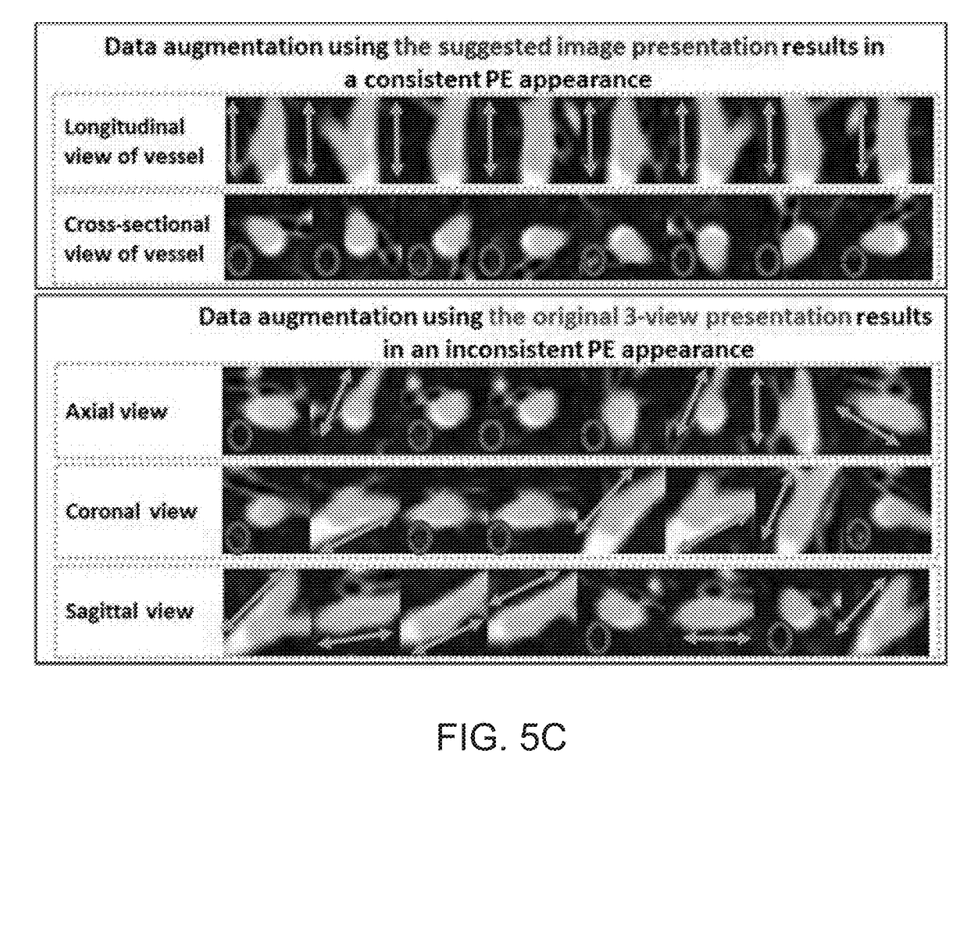
FIG. 5C is an illustration comparing the appearance of pulmonary embolisms using traditional imaging views and a vessel-aligned image representation in view of data augmentation, in accordance with aspects of the present disclosure

The image representation described herein further supports data augmentation, which is important for effective training and testing of CNNs. In 2D applications, data augmentation is performed by collecting samples at multiple scales (image pyramid), extracting samples from locations with slight translations from the actual candidate location, and applying arbitrary in-plane rotations to the collected samples. A 3D representation must also support the above operations in order to enable data augmentation. While it may be straightforward to extend translation and scaling to 3D space, the rotation operation can be problematic. The vessel-aligned image representation herein is based on longitudinal and cross-sectional planes. Rotating such plus along a random axis would result in an arbitrary appearance of the same PE in the resulting images, as illustrated in FIG. 5A. Therefore, a major challenge is how to perform 3D rotation in the resulting 2-channel images so that the PE representation remains consistent because rotating planes along a random axis can result in the arbitrary appearance of the same PE. The presently described image representation accommodates this need by rotating the planes around the vessel axis $v_1$. By doing so, a large number of additional instances can be generated while retaining the consistency. In particular, two envelopes of image planes, as illustrated in FIG. 5B are obtained, where the first envelope contains the planes that all intersect at the vessel axis, and the second envelope contains the image planes whose normals are the vessel axis. By selecting any pairs of planes from the two envelopes, one can generate a new PE instance while retaining consistence. FIG. 5C illustrates variations in PE appearances when using arbitrary axes compared to vessel axes.

In addition to descriptions above, specific examples are provided below, in accordance with the present disclosure. These examples are offered for illustrative purposes only, and are not intended to limit the scope of the present invention in any way. Indeed, various modifications in addition to those shown and described herein will become apparent to those skilled in the art from the foregoing description and the following example and fall within the scope of the appended claims.

EXAMPLE

The present approach was tested using 121 CTPA datasets with a total of 326 emboli, achieving a sensitivity of 83% at 2 false positives per volume. This performance is shown to be superior to the best performing CAD system in the literature, which at best achieves a sensitivity of 71% at the same level of false positives. The present approach was further evaluated with the entire 20 CTPA testing datasets from the PE challenge, outperforming a best reported performance—MeVis', at 0 mm localization error. The present approach was evaluated using 2 databases: (1) a proprietary database consisting of 121 CTPA datasets with a total of 326 emboli, and (2) the test database of the PE challenge (www.cad-pe.org) consisting of 20 CTPA datasets with a total of 133 emboli.

Evaluations Using the Proprietary Database.

The candidate generation module of a CAD system, in accordance with the present disclosure, produced a total of 8585 PE candidates in the 121 CTPA datasets of which 7722 were false positives and 863 were true positives. Of note is that the number of true detections were more than the number of PEs in the database because it is possible for a CAD system to produce multiple detections for a large PE. According to the available ground truth, the candidate generation module achieved a sensitivity of 93% to PEs while producing on average 65.8 false positives per patient.

As described, CNNs can be used to minimize the number of false positives while maintaining a high sensitivity to PEs. To train CNNs, the collected detections were randomly split at patient level in 3 groups, enabling a 3-fold cross validation of the CAD system. The false positive detections were then used as negative candidates and the true detections as positive candidates. Given the limited number of candidates, the training set was formed by performing data augmentation. For this purpose, N=Nr×Nt×Ns samples were collected from each candidate location based on a vessel-aligned multi planar PE representation, where Nr was the number of rotations, Nt was the number of translations, and Ns as the number of image scaling.

To produce rotated patches, the longitudinal and cross-sectional vessel planes were rotated around the vessel axis Nr=5 times. For scaling, patches at Ns=3 were extracted at different scales, resulting in 10 mm, 15 mm, and 20 mm wide patches. In each scale, an image interpolation was performed so that the resulting patches were all 32×32 pixels. For translation, the candidate location was shifted along the vessel direction Nt=3 times by up to 20% of the physical width of the patches. With data augmentation, the size of the training set could be increased by a factor of N=30, which was sufficiently large to train CNNs. Given a test dataset, a set of candidates was first obtained, and then the trained CNNs were applied on N 2-channel image patches extracted from each candidate location. The confidence values for the underlying candidate were then computed as the average of the resulting N confidence values. Once all the test candidates were processed, the threshold on the corresponding confidence values was changed to obtain a free-response receiver operating characteristic ("FROC") curve.

Figure 6:
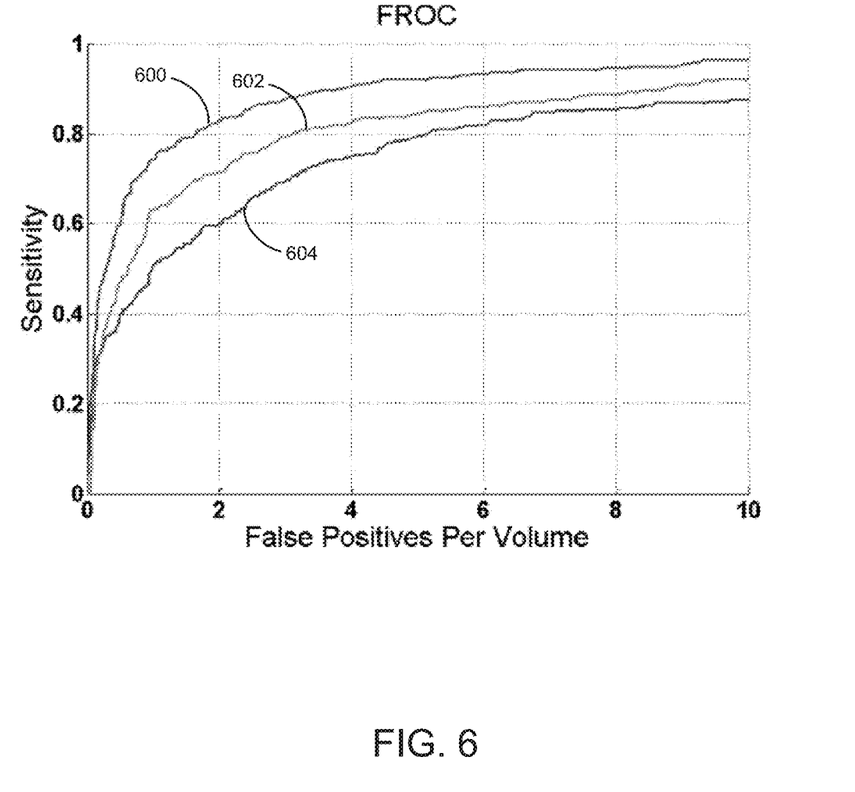
FIG. 6 is a graph comparing sensitivity versus false positive detection for the present approach relative to previous techniques.

FIG. 6 shows the FROC curve obtained using the present approach 600. For comparison, FROC curves based on prior methods are also plotted in FIG. 6. In particular, these prior methods were chosen given that they achieve the best performance to date as reported in the literature using a reasonably large CTPA database (see Table 1). As appreciated from the figure, the CAD system based the herein described image representation outperforms the best hand-crafted approach 604 and also a CNN powered by a 2.5 D approach 602.

In particular, the present CAD system outperformed previously reported methods, demonstrating the superiority of the suggested PE representation and CNNs over a carefully designed set of hand-crafted features and a multi-instance classifier. In addition, a CNN was trained using 3-channel patches obtained through a 2.5 D image representation as suggested in a prior method. In the 2.5 D approach, patches were extracted from sagittal, axial and coronal views (no vessel alignment), and data augmentation was performed with respect to some random vectors (not vessel axis). Although this approach was found suitable for detecting lymph nodes mainly due to their spherical shapes, such an image representation was not suitable for PE detection because PEs appear in a variety of shapes and orientations.

Referring again to FIG. 6, replacing the present image representation with a 2.5 D approach resulted in a performance which was not only inferior but also to the hand-crafted approach, demonstrating the significant contribution of our effective image representation in achieving the improved performance. Table 1 contrasts the performance of the suggested CAD system with that of other CAD systems suggested in the literature.

TABLE 1

(top) Performance of the existing PE CAD systems obtained through different datasets. (bottom) Performance comparison based on the proprietary database of 121 CTPA datasets. Operating points are taken from FIG. 6.

| Method | Sensitivity | FPs/vol | #datasets | #PEs |
|---|---|---|---|---|
| Liang et al. | 70.0% | 2.0 | 132 | 716 |
| Bouma et al. | 58% | 4.0 | 19 | 116 |
| Park et al. | 63.2 | 18.4 | 20 | 44 |
| Ozkan et al. | 61% | 8.2 | 33 | 450 |
| Wang et al. | 62% | 17.1 | 12 | 24 |
| This work | 83.4% | 2.0 | 121 | 326 |
| This work (2.5D) | 60.4% | 2.0 | 121 | 326 |
| Liang et al. | 71.7% | 2.0 | 121 | 326 |

Evaluations Using PE Challenge Database.

A CNN, powered by the image representation as disclosed herein, was further trained using all 121 CTPA datasets from the proprietary database and then evaluated our CAD system using the test database from the PE challenge. Since the ground-truth was not available on the website, detection results were evaluated by the organizers. At 0 mm localization error, the present CAD system achieved a sensitivity of 34.6% at 2 FPs/vol, which outperformed the winning team (a commercial CAD system designed MeVis Medical Solutions) with a sensitivity of 28.4% at the same false positive rate. Of note is that the present CAD system exhibited a discernible performance degradation compared to the results obtained using the proprietary database. This may be caused by faulty lung segmentation that results in PE candidates in the colon and diaphragm.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for detecting pulmonary embolisms in a subject's vasculature, the system comprising:
an input configured to receive images acquired from a subject;
a processor configured to process the images with steps comprising:
   i. receiving, using the input, a set of images representing a vasculature of the subject;
   ii. analyzing the set of images to identify pulmonary embolism candidates associated with the vasculature;
   iii. generating, for identified pulmonary embolism candidates, image patches based on a vessel-aligned image representation;
   iii. applying a set of convolutional neural networks to the generated image patches to identify pulmonary embolisms;
   vi. generating a report indicating identified pulmonary embolisms; and
an output for displaying the report.

2. The system of claim 1, wherein the set of images comprises computed tomography pulmonary angiography ("CTPA") images.

3. The system of claim 1, wherein the set of images comprises three-dimensional ("3D") images.

4. The system of claim 1, wherein the processor is further configured to execute a tobogganing algorithm to identify the pulmonary embolism candidates.

5. The system of claim 1, wherein the vessel-aligned image representation comprises a longitudinal view and a cross-sectional view of vessels associated with identified pulmonary embolism candidates.

6. The system of claim 1, wherein the processor is further configured to determine an orientation of vessels associated with identified pulmonary embolism candidates to determine the vessel-aligned image representation.

7. The system of claim 6, wherein the processor is further configured to determine the orientation by performing vessel orientation analysis based on a principle component analysis.

8. The system of claim 6, wherein the processor is further configured to determine the orientation by using a structure tensor or a Hessian matrix.

9. A method for detecting pulmonary embolisms in a subject's vasculature, the system comprising:
acquiring a set of images representing a vasculature of the subject;
analyzing the set of images to identify pulmonary embolism candidates associated with the vasculature;
generating, for identified pulmonary embolism candidates, image patches based on a vessel-aligned image representation;
applying a set of convolutional neural networks to the generated image patches to identify pulmonary embolisms; and
generating a report indicating identified pulmonary embolisms.

10. The method of claim 9, wherein the set of images comprises computed tomography pulmonary angiography ("CTPA") images.

11. The method of claim 9, wherein the set of images comprises three-dimensional ("3D") images.

12. The method of claim 9, wherein the method further comprises executing a tobogganing algorithm to identify the pulmonary embolism candidates.

13. The method of claim 9, wherein the vessel-aligned image representation comprises a longitudinal view and a cross-sectional view of vessels associated with identified pulmonary embolism candidates.

14. The method of claim 9, wherein the method further comprises determining an orientation of vessels associated with identified pulmonary embolism candidates to determine the vessel-aligned image representation.

15. The method of claim 14, wherein the method further comprises determining the orientation by performing a vessel orientation analysis based on a principle component analysis.

16. The method of claim 14, wherein the method further comprises determining the orientation by performing a vessel orientation analysis using a structure tensor or a Hessian matrix.

* * * * *